(12) United States Patent
Billingham (10) Patent No.: US 6,348,497 B1
(45) Date of Patent: Feb. 19, 2002

(54) COMPOUNDS WHICH INTERACT WITH THE THYROID HORMONE RECEPTOR FOR THE TREATMENT OF FIBROTIC DISEASE

(75) Inventor: Michael Edward John Billingham, Hants (GB)

(73) Assignee: Arthromics plc, Manchester (GB)

( * ) Notice: Subject to any disclaimer, the term of this patent is extended or adjusted under 35 U.S.C. 154(b) by 0 days.

(21) Appl. No.: 09/674,512

(22) PCT Filed: May 27, 1999

(86) PCT No.: PCT/GB99/01684

§ 371 Date: Nov. 16, 2000

§ 102(e) Date: Nov. 16, 2000

(87) PCT Pub. No.: WO99/62507

PCT Pub. Date: Dec. 9, 1999

(30) Foreign Application Priority Data

Jun. 2, 1998 (GB) ............................................. 9811784
Dec. 17, 1998 (GB) ............................................. 9827834

(51) Int. Cl.[7] ........................ A61K 31/19; A61K 31/195
(52) U.S. Cl. ........................................ 514/570; 514/567
(58) Field of Search .................................. 514/570, 567

(56) References Cited

FOREIGN PATENT DOCUMENTS

| EP | 0 009 306 | 4/1980 |
|----|-----------|--------|
| EP | 0 037 698 | 10/1981 |
| GB | 860 303 | 5/1959 |
| GB | 1140748 | 5/1967 |
| WO | WO92/05447 | 4/1992 |
| WO | WO95/27202 | 10/1995 |
| WO | WO96/01430 | 1/1996 |
| WO | WO97/35195 | 9/1997 |

OTHER PUBLICATIONS

"Effects of commonly prescribed nonsteroidal anti–inflammatory drugs on thyroid hormone measurements", Bishnoi et al, Am. J. Med., 1994, 96(3), 235–8: Abstract.*

"The nuclear receptor corepressor SMRT inhibits collagenase (MMP–1) transcription through an HRE–independent mechanism", Schroen et al, Biochemical and Biophysical Research Comm., 1997 (Aug. 8), 237(1), 52–8: Abstract.*

\* cited by examiner

*Primary Examiner*—Zohreh Fay
*Assistant Examiner*—Brian-Yong Kwon
(74) *Attorney, Agent, or Firm*—Martin A. Hay (57) ABSTRACT

A method of alleviating loosening of prosthetic joints by administering an effective amount of at least one compound having the formula (I)

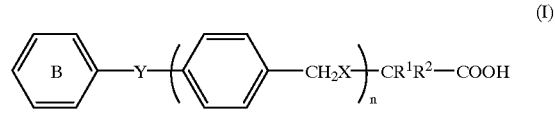

in which X stands for the oxygen or sulphur atom or for the imino (—NH—) or sulphonyl (—SO$_2$—) radical, Y stands for a direct linkage, or for the oxygen or sulphur atom or for the sulphonyl (—SO$_2$—) radical or for the radical of the formula —CR$^1$R$^2$—, wherein R$^1$ and R$^2$ which may be the same or different are hydrogen, alkyl or aryl radicals or R$^1$ and R$^2$ may be joined together to form a cycloalkyl ring, n is an integer having the value 0 or 1, provided that when n is 0, Y stands for the oxygen or sulphur atom or for the sulphonyl (—SO$_2$—) radical, or an ester, amide or salt thereof.

5 Claims, 9 Drawing Sheets

Figure 1A:
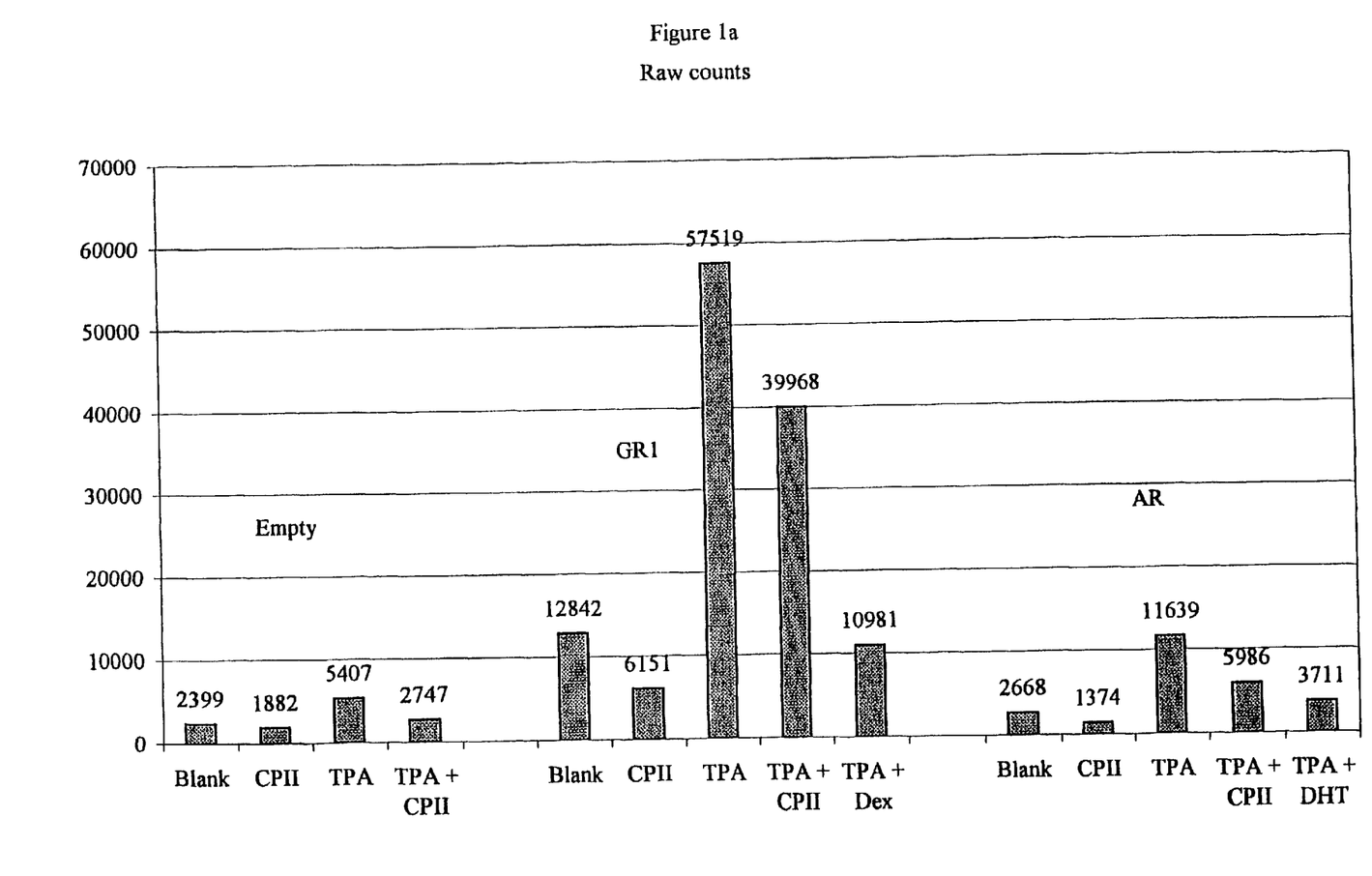

Figure 1a
Raw counts

Figure 1B:
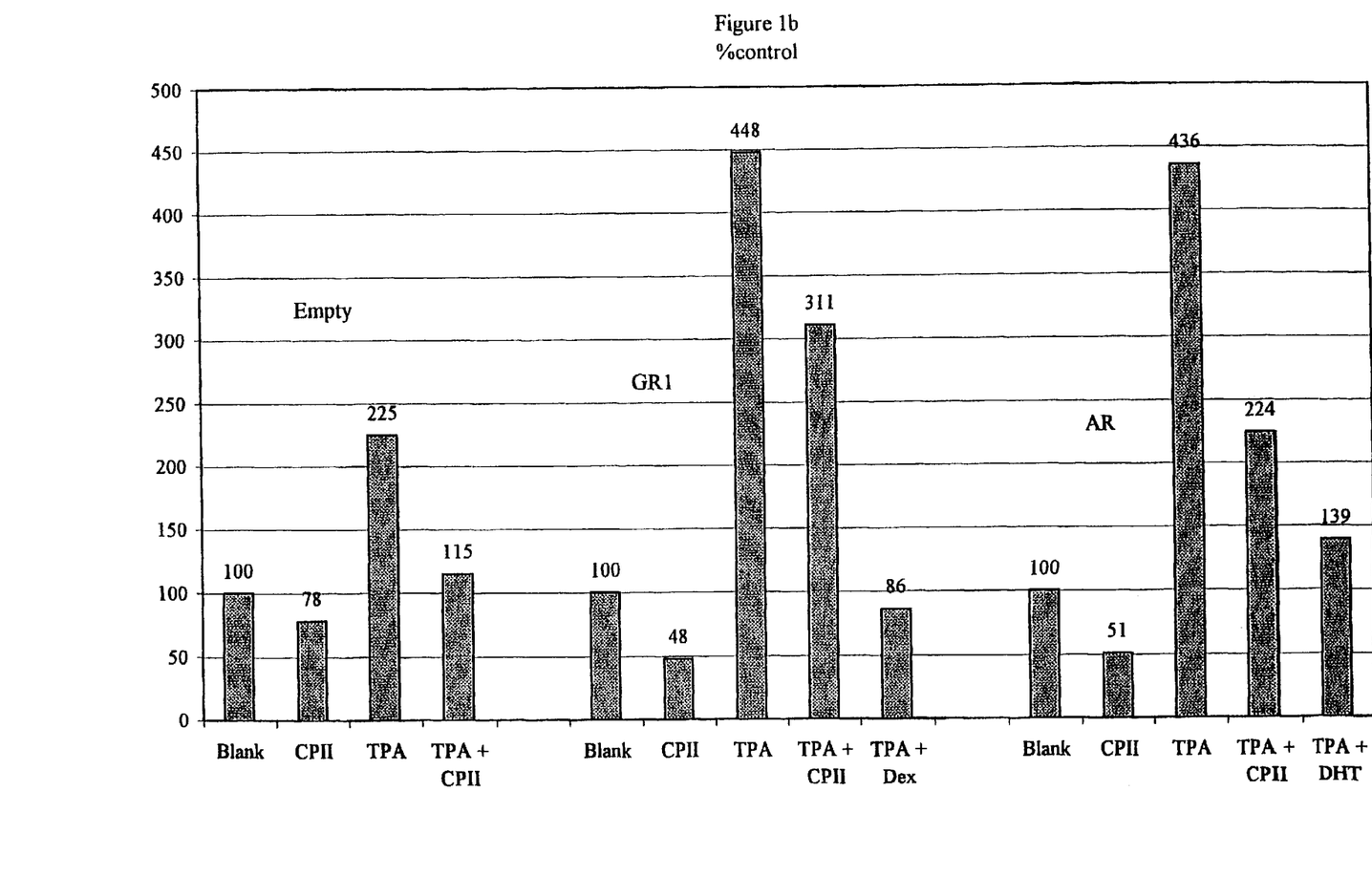

Figure 1b
%control

Phospho-c-jun          MMP-1

1   2   3   4          5   6   7   8

⇐ pro-MMP-1
⇐ active MMP-1

COMPOUNDS WHICH INTERACT WITH THE THYROID HORMONE RECEPTOR FOR THE TREATMENT OF FIBROTIC DISEASE

This application is the national stage of application Ser. No PCT/GB9910/684, filed on May 27, 1999.

This invention relates to fibrotic diseases.

There are many fibrotic diseases in the human. These are sometimes referred to as chronic connective tissue diseases, and include degradative and proliferative conditions. They include, for example, deterioration of the joints in arthritis, deformation of vessel walls in artherosclerosis, accelerated cardiovascular problems associated with diabetes, lung fibrosis and cirrhosis of the liver. These fibrotic diseases are generally considered and studied as separate and different problems However, it is possible that common pathways exist in all these fibrotic diseases. Indeed, corticosteriods are used in the treatment of many of these diseases to relieve symptoms and prevent associated tissue destruction and scarring; however, the use of corticosteroids is associated with dose and treatment duration side-effects which limit the usefulness of this type of compound.

Some fibrotic diseases are particularly distressing, such as, for example, those involving deterioration of cartilage and bone in the joint. Amelioration of such diseases is a particularly difficult target for the pharmaceutical industry. These conditions are often accompanied by distressing levels of pain and gradual impairment of structural body function and movement. An added difficulty in attempting to find a satisfactory cure or improvement is that joint disease appears to be largely species specific. Therefore, research into joint disease in man is made more difficult in that animal models may not be appropriate.

In mankind, joint disease is generally progressive and affects all ages, but is particularly prevalent in middle and old age. Quality of life of the patient is severely reduced as the level of pain and reduction in mobility increase. Treatments hitherto have, therefore, been directed at manifestations of the disease or malfunction which are comparatively less difficult to treat. In rheumatoid arthritis, these include symptom-modifying anti-rheumatic drugs (so-called SMARD) for the relief of pain and decrease in inflammation at the joint or in the synovial membrane, such as, for example, non-steroidal anti-inflammatory drugs (so-called NSAID). Some drugs are said to be disease modifying (so-called DMARD), such as, for example, non-cytotoxics such as anti-malarials, gold, sulphasalazine, D-penicillamine, and cytotoxics such as cyclophosphamide and chlorambucil. However, such drug treatments are often associated with unpleasant or undesirable side effects, which limit their application and utility. A new category of anti-rheumatic drugs, Disease Controlling Anti-Rheumatic Drugs, (so-called DCARD) has been proposed to describe drugs that effectively control the destructive processes but as yet no marketed anti-rheumatic drugs merit this classification, although corticosteroids have some inhibitory effect on the articular damage at the low doses that can be tolerated for long term treatment.

However, consideration of the above fibrotic diseases as a class having a common pathway may prove valuable in attempting to invent new treatments.

It is known that corticosteriods can regulate gene transcription by binding to their specific receptor which is one member of the steroid receptor super-family (Physiology of the steroid-thyroid hormone nuclear receptor superfamily. Williams G R, Franklyn J A. Bailliére's Clinical Endocrinology and Metabolism Vol 8 No 2 pp241–266 1994). This super-family includes the glucocorticoid, oestrogen, progesterone, androgen, thyroid hormone, Vitamin D and retinoic acid receptors. Such receptors are responsible for the regulation of many genes including those encoding tissue destructive proteolytic enzymes, for example, metalloproteinases (sometimes referred to as MMPS). One such MMP is collagenase 1. Corticosteroids interact specifically with the corticoid receptor which then binds to the promoters of the genes. This liganded corticosteroid receptor represses activation of the collagenase gene by modulating the activity of transcription factor AP-1 (activating protein 1, heterodimer of c-fos and c-jun proteins; reviewed by Cato and Wade BioEssays Vol 18 No 5 pp371–378 1996). The liganded steroid receptor thus modulates production of protein destructive enzymes, thereby reducing degradation of joint tissues such as cartilage and bone.

Many of the members of the superfamily of steroid receptors can modulate tissue destructive proteolytic enzyme production when liganded with the natural hormone. However, use of the natural hormone at pharmacological levels is associated with severe side effects due to their biological activity in many physiological systems. Corticosteroids effectively inhibit proteolytic enzyme production at the transcriptional level, through modulation of AP1, but the problem with corticosteroids is that they have additional transactivation effects on genes that lead to side effects, such as bone osteoporosis, diminishment of the immune response and water retention. Some of these side effects can be life threatening. Therefore, such inhibition or modulation in the substantial absence of the above hitherto undesirable associated side effects would represent a major therapeutic advance.

These undesirable additional transactivation effects are surprisingly substantially avoided in accordance with the present invention. It has been found that the use of the compounds described below have substantially no transactivation properties and do not transrepress body defence mechanisms signalled by immune hormones such as the cytokines, IL1 and TNF and the early response transcription factor NFκB (Mukaida N et al, J Biol Chem, 269, 13289–13295, 1994). The compounds below, and their associated pharmaceutical compositions, are not likely, therefore, to compromise the immune system, which is one of the one of the major problems associated with the use of corticosteroids. This is a surprising finding and clearly separates this class of molecule from the conventional steroid hormones.

It has been found that compounds (I) hereinafter described are able to regulate MMP gene activation, but surprisingly not through occupation of either the corticosteroid receptor or the androgen receptor. Therefore, surprisingly compounds (I) appear to regulate MMP gene activation through a different receptor and hence compounds (I) can thereby substantially prevent transcription of NMP, including collagenase 1.

Indeed, it has been further found that compounds (I) acts through occupation of the thyroid hormone receptor. Herein lies the basis of the present invention.

Thus according to the present invention, a method is provided of alleviating fibrotic disease by regulating tissue destructive proteolytic enzyme production in the presence of thyroid receptor binding, but in the substantial absence of substantive corticosteroid and androgen receptor binding. This is effected by administration of an effective amount of at least one compound having the formula (I)

(I)

in which X stands for the oxygen or sulphur atom or for the imino (—NH—) or sulphonyl (—SO$_2$—) radical, Y stands for a direct linkage, or for the oxygen or sulphur atom or for the sulphonyl (—SO$_2$—) radical or for the radical of the formula —CR$^1$R$^2$—, wherein R$^1$ and R$^2$ which may be the same or different are hydrogen, alkyl or aryl radicals as hereinafter described, ring B may be optionally substituted by one or more substituents selected from halogen atoms and alkyl and aryl radicals, n is an integer having the value 0 or 1, and esters, amides and salts thereof

In the compounds having the formula (I), R$^1$ and R$^2$ may be the same or different and preferably R$^1$ is selected from hydrogen or 1–4C alkyl, and R$^2$ from hydrogen, 1–4C alkyl or phenyl (which may be optionally substituted with at least one halogen atom, for example, chlorine, bromine), and R$^1$ and R$^2$ may be joined together to form a cycloalkyl ring (for example, cyclohexyl); the ring B may be optionally contain one or more substituents selected from halogen atoms and 1–4C alkyl. Most preferably, the 1–4C alkyl radicals are methyl or ethyl, and the halogen atom is chlorine.

Esters of compound (I) may be useful in the present invention. Such esters are preferably derived from alcohols having the formula R$^3$—OH, where R$^3$ is preferably 1–4C alkyl, most preferably methyl or ethyl. Salts of compound (I) include alkali metal and alkaline earth salts, and include magnesium, aluminium, bismuth, ammonium, and preferably sodium, potassium and calcium. Where the compound (I) contains a strongly basic substituent, acid addition salts thereof, such as the hydrochloride, are comprehended.

Compounds having the formula (I), in which n is 1, and R$^1$ and R$^2$ which may be the same or different are hydrogen or alkyl radicals, are described in United Kingdom patent specification 1140748, the disclosure of which is incorporated herein. Such compounds are considered to be useful in the treatment or prophylaxis in humans and animals of such diseases as coronary artery disease and atherosclerosis. This is because they are said to reduce the concentration of cholesterol and/or triglycerides in the blood serum and the level of fibrinogen in blood plasma of rats. They are also said to possess anti-inflammatory activity in rats, and are, therefore, considered to be useful in the treatment of inflammatory signs and symptoms such as rheumatoid arthritis in man; further work has shown that such compounds have substantially no anti-inflammatory properties (Billingham MEJ and Rushton A, Anti-inflammatory and Anti-arthritic Drugs, Vol III, Edited by. K D Rainsford, 31–63, 1985, CRC Press)). A particularly preferred compound, 1-[4-(4-chlorophenyl)benzyloxy]-1-methylpropionic acid, has the formula (II)

(II)

European patent specification 0 037 698, the disclosure of which is incorporated herein, describes processes for the production of compounds having the formula (I) in which n takes the value 1, Y is a direct link and R$^1$ and R$^2$ which may be the same or different are hydrogen or (1–4C) alkyl. A preferred compound has the formula (III).

(III)

United Kingdom patent specification 860303, the disclosure of which is incorporated herein, describes compounds having the formula (I) in which n takes the value 0. A preferred compound has the formula (IV) and is known as clofibrate.

(IV)

According to the present invention a method of modifying fibrotic disease in warm blooded animals is provided which comprises administering the animal an effective amount of at least one compound having the formula (I). In a further embodiment of the present invention a pharmaceutical composition is provided containing at least one compound having the formula (I) for the structural modification of fibrotic tissue in a warm blooded animal.

In accordance with the present invention, many fibrotic and proliferative conditions are considered to gain benefit from treatment with the pharmaceutical composition. These include, for example, rheumatoid arthritis, psoriatic arthritis and psoriasis itself, the loosening of prosthetic joints, atherosclerosis of cardiac and coronary vessels and large arteries, the complications of diabetes, lung fibrosis, liver cirrhosis, systemic sclerosis, muscular dystrophy.

In order to be useful in the treatment of the above conditions in accordance with the present invention, the above compounds may be administered as a pharmaceutical composition by any suitable route, but preferably orally, as, for example, tablets, capsules, suspension, emulsions, powders, syrups, elixirs. They may be administered as suppositories. The pharmaceutical compositions may be formulated to include any pharmaceutically acceptable excipient and may be prepared by any suitable method known on the art, such as those described in any of the above patent specifications. The compositions should preferably be administered to ensure that the patient receives between 0.01 g and 0.5 g of active ingredient per day, the composition containing suitably between 0.01 g and 0.5 g of active ingredient.

The invention is illustrated with reference to the following experimental information.

Two plasmid constructs were introduced by standard calcium phosphate precipitation of DNA followed by glycerol shock (Ausubel F M, Brent R, Kingston D D, Moore J G et al Current protocols in molecular biology 1994 Greene Publishing Associates/Wiley-Interscience, New York, N.Y.) using a transformed African Green Monkey kidney cell line (CV1) (Schneikert J, Peterziel H, Defossez P-A, Klocker H, de Launoit Y and Cato ACB Androgen receptor-Ets protein interaction is a novel mechanism for steroid hormone-mediated down-modulation of matrix metalloproteinase expression. Journal of Biological Chemistry. Vol 271(39) (pp 23907–23913), 1996).

EXPERIMENT 1

This experiment was intended to show reduction in MMP promoter activity. Accordingly, the following two plasmids were included into CV1 cells described above (a) Either of GR1 or pSG5ARF containing glucocorticoid or androgen receptor (AR) respectively, both at 2 ug per $5\times10^5$ cells, driven by the Rous sarcoma virus promoter, and (b) a plasmid containing the −73/+63 portion of the collagenase I promoter linked to luciferase gene at 8 ug per $5\times10^5$ cells.

These cells were stimulated using TPA (12-O-tetradecanoylphorbol-13-acetate) at 75 ng/ml, which enhanced the activity of the collagenase promoter. The stimulation increased luciferase production, which was measured by luminescence after addition of the luciferase substrate (luciferin) and co-factors.

The blank represented the inclusion of these two plasmids alone with little endogenous activation of collagenase. Addition of TPA stimulated the activity of this promoter region, resulting in a high level of luciferase production which is eventually seen as an enhancement in fluorescence (Y-axis). Both dihydroxytestosterone (DHT) at $10^{-7}$M and dexamethazone (Dex) at $10^{-7}$M were able to down regulate this activation through their respective receptors. CPII was compound II above, clobuzarit. "Empty" indicated the results when neither GR1 or AR receptors were present. The results are presented in Table 1.

TABLE 1

|  | Empty | | GR1 | | AR | |
| --- | --- | --- | --- | --- | --- | --- |
|  | Raw counts | % control | Raw counts | % control | Raw Counts | % control |
| Blank | 2399 | 100 | 12842 | 100 | 2668 | 100 |
| CPII | 1882 | 78 | 6151 | 48 | 1374 | 51 |
| TPA | 5407 | 225 | 57519 | 448 | 11639 | 436 |
| TPA + CPII | 2747 | 115 | 39968 | 311 | 5986 | 224 |
| TPA + DHT |  |  |  |  | 3711 | 139 |
| TPA + Dex |  |  | 10981 | 86 |  |  |

The above results are presented graphically in FIGS. 1a and 1b. From the results in Table 1, it is shown that Compound II was also, in addition to DHT or Dex, able to down regulate collagenase I activation, and also to inhibit partially the background level of collagenase promoter activity. The level of this reduction which is achieved by the use of Compound II in both stimulated and unstimulated conditions is similar, when expressed as ratio of luciferase counts seen without inclusion of this molecule, over observable counts when Compound II is included. This suggests that Compound II does not require the presence of either receptor in order to exert its action. This is further supported by the observation that Compound II is able to reduce the level of both TPA stimulated and unstimulated collagenase I (MMP) promoter activity in the absence of either receptor (Empty).

EXPERIMENT 2

This experiment was intended to investigate the activation of androgen and corticosteroid receptors by compound I.

The CV1 cells described above were transfected with the following two plasmids (a) PGL3NMMTV plasmid, containing a transcription site which is activated by the androgen and glucocorticoid receptor, linked to the luciferase gene at 9 ug per $5\times10^5$ cells, and (b) either one of the plasmids GR1 or pSG5ARFin, containing glucocorticoid or androgen receptor (AR) respectively, under the control of constitutively active promoters, both at 2 ug per $5\times10^5$ cells.

The blank represented the inclusion of these two plasmids alone, resulting in the absence of receptor activity. Inclusion of dihydroxytestosterone (DHT) at $10^{-7}$M or dexamethazone (Dex) at $10^{-7}$M to the culture medium enabled the receptor to stimulate the transcription of the promoter region linked to luciferase which was eventually seen as an enhancement in fluorescence (Y-axis). CPII was compound II above, clobuzarit, which was used at $10^{-7}$M.

TABLE 2

|  | Raw counts | % control |
| --- | --- | --- |
| AR | | |
| Blank | 4637 | 100 |
| DHT | 1731765 | 37347 |
| CPII | 33130 | 714 |
| DHT + CPII | 1232241 | 26574 |
| GR1 | | |
| Blank | 3569 | 100 |
| Dex | 619085 | 17346 |
| CPII | 3272 | 92 |
| Dex + CPII | 748249 | 20965 |

Figure 2A:
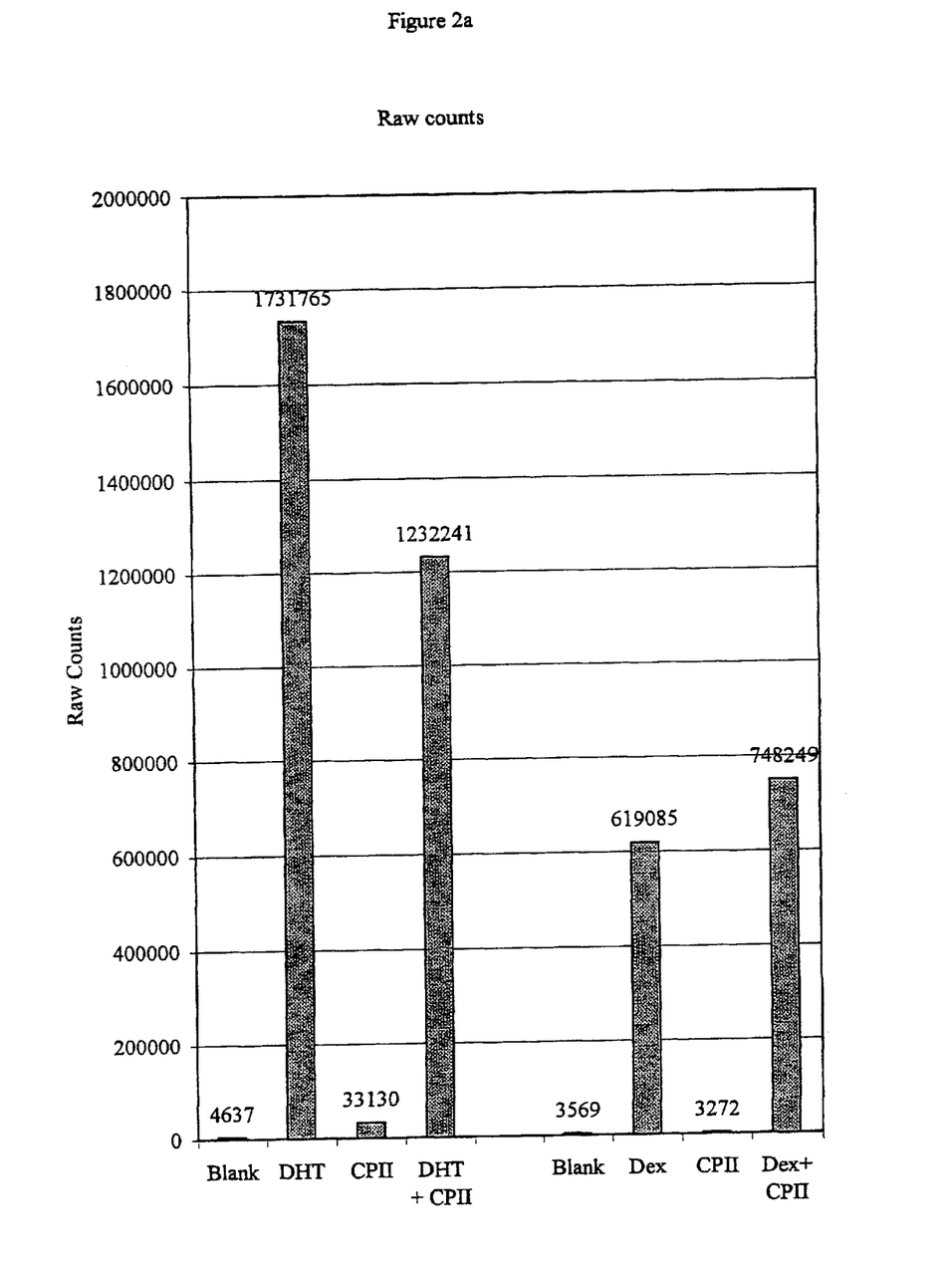
Figure 2B:
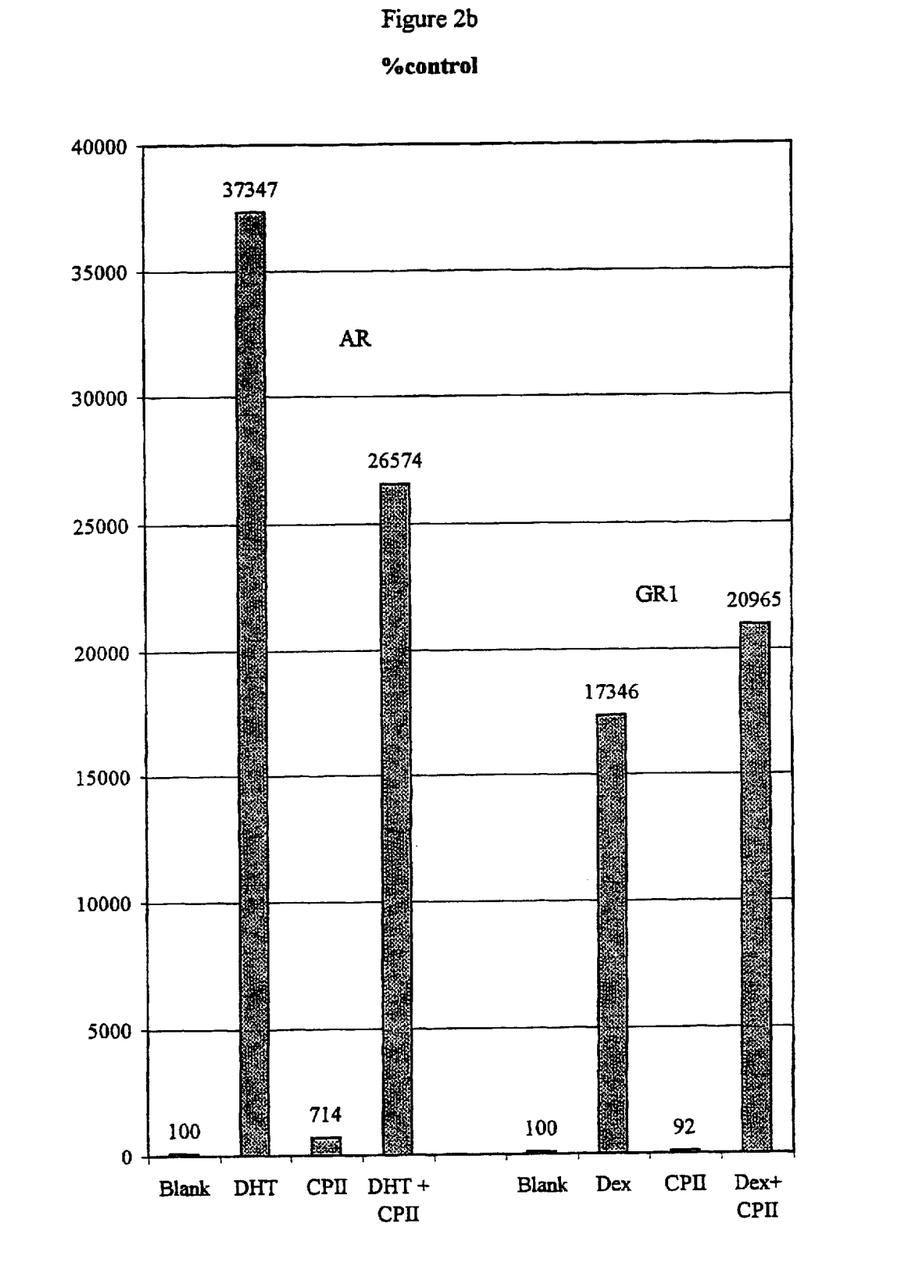

The above results are presented graphically in FIGS. 2a and 2b. From the results in Table 2, it is shown that Compound II shows negligible activity to activate the same mechanism as that produced by the addition of the two steroids DHT and Dex.

EXPERIMENT 3

This experiment was intended to show the effect of compounds I on a mediator of the immune response, nuclear factor –κB (NF-κB).

The following two plasmids were included into CV1 cells described above (a) GR1 as described above at 2 ug per $5\times10^5$ cells, and (b) a plasmid designated 3-EnhTK-Luc (at 0.5 ug per $5\times10^5$ cells) which contains a transcription site that is activated by NFκB. The cells themselves are capable of synthesising this protein and hence it is not necessary to transfect this as well.

The blank represented the inclusion of these two plasmids alone; the relatively high value was caused by (i) the high level of serum in the culture, and (ii) the associated stress that the cells underwent during the transcription process—both of which upregulate NFκB. There was also a related relatively low activation of TNF (at 4 ng/ml) above a serum containing blank in the experiment. TNF was tumour necrosis factor alpha.

TABLE 3

|  | Raw counts | % control |
| --- | --- | --- |
| Blank | 59538 | 100 |
| CPII | 75812 | 127 |
| TNF | 82579 | 139 |
| TNF + CPII | 135886 | 228 |
| TNF + Dex | 18525 | 31 |

Figure 3:
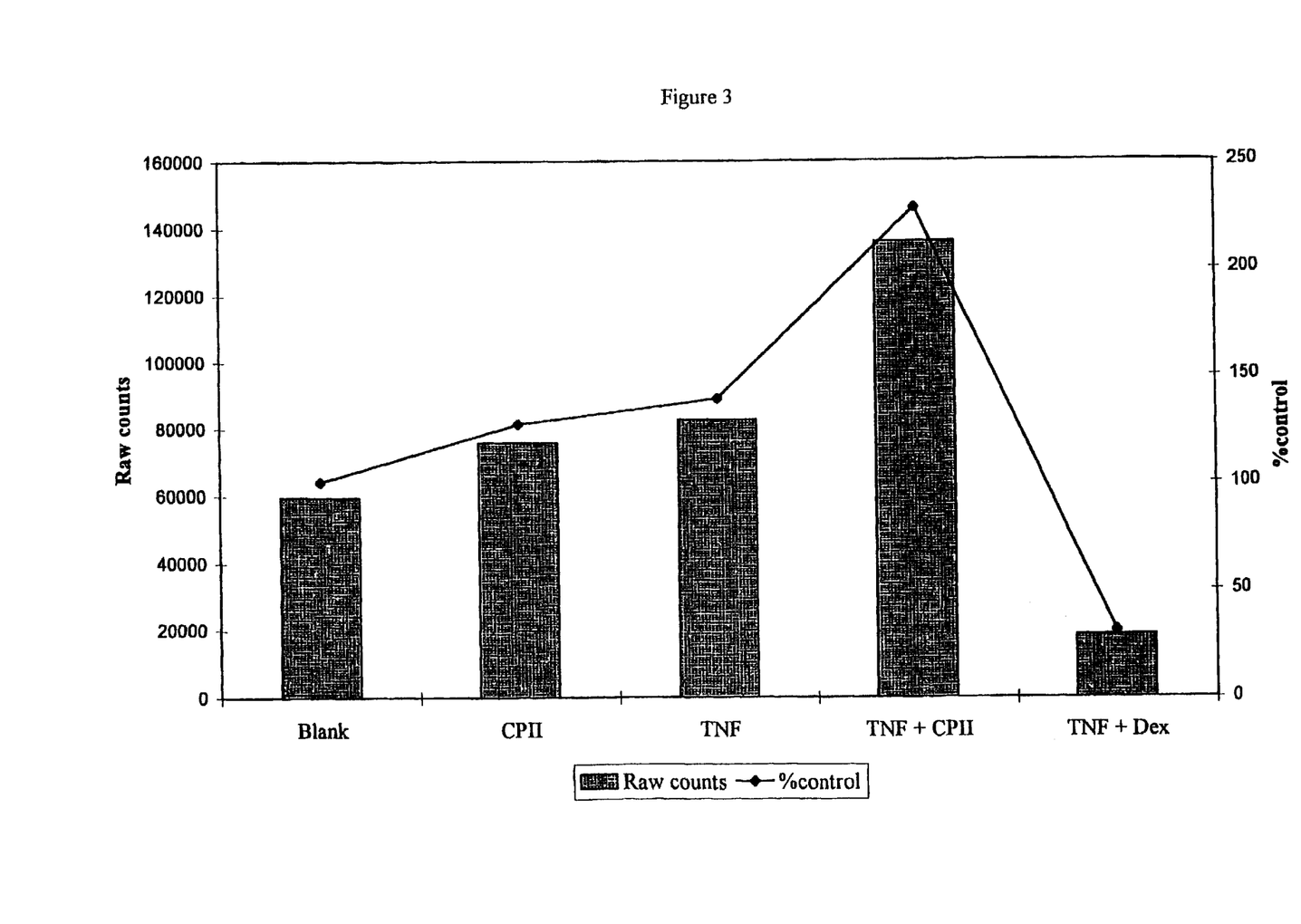

The above results are presented in FIG. 3. The results show that Compound II shows little variation from the background value, indicating that it is not able to upregulate transcriptional activity by NFκB. The lack of inhibitory effect of Compound II on NFκB transcription is in contrast to the marked effect of Dex, showing that Compound II does not act as an anti-inflammatory agent, so supporting the earlier clinical data. Also, from the lack of substantive stimulation, it can also be inferred that Compound II, in contrast to DEX, does not interfere with immune response signalling.

EXPERIMENT 4

These experiments were intended to identify the receptor through which compounds I might be acting to block collagenase promoter activity.

Transfection procedure hereinbefore described with CV1 cells was repeated using MCF-7 mammary breast cancer cells derived from pleural effusion from a breast cancer patient. Additionally, each experiment included transfection of a plasmid (at 8 ug per $5 \times 10^5$ cells) containing the −517/+63 section of the collagenase (MMP- 1) promoter linked to the luciferase gene. TPA was used as above to stimulate activity of the collagenase promoter resulting in luciferase production. Compound II or 3,3,5-triiodo-L-thyronine (T3) was included (both at $10^{-8}$M), the latter being a known ligand for the thyroid hormone receptor.

A series of three experiments was then carried out.

EXPERIMENT 4.1.

As MCF-7 cells express endogenous thyroid hormone receptors, only the collagenase promoter plasmid ( at 8 ug per $5 \times 10^5$ cells) was transfected into the MCF-7 cells.
The results are shown in Table 4. 1.

TABLE 4.1

|  | Raw Counts | % Control |
| --- | --- | --- |
| Blank | 12575 | 100 |
| CPII | 6029 | 47.9 |
| TPA | 147665 | 1174.3 |
| TPA + T3 | 428062 | 3404.1 |
| TPA + CPII | 352376 | 2802.2 |

Figure 41:
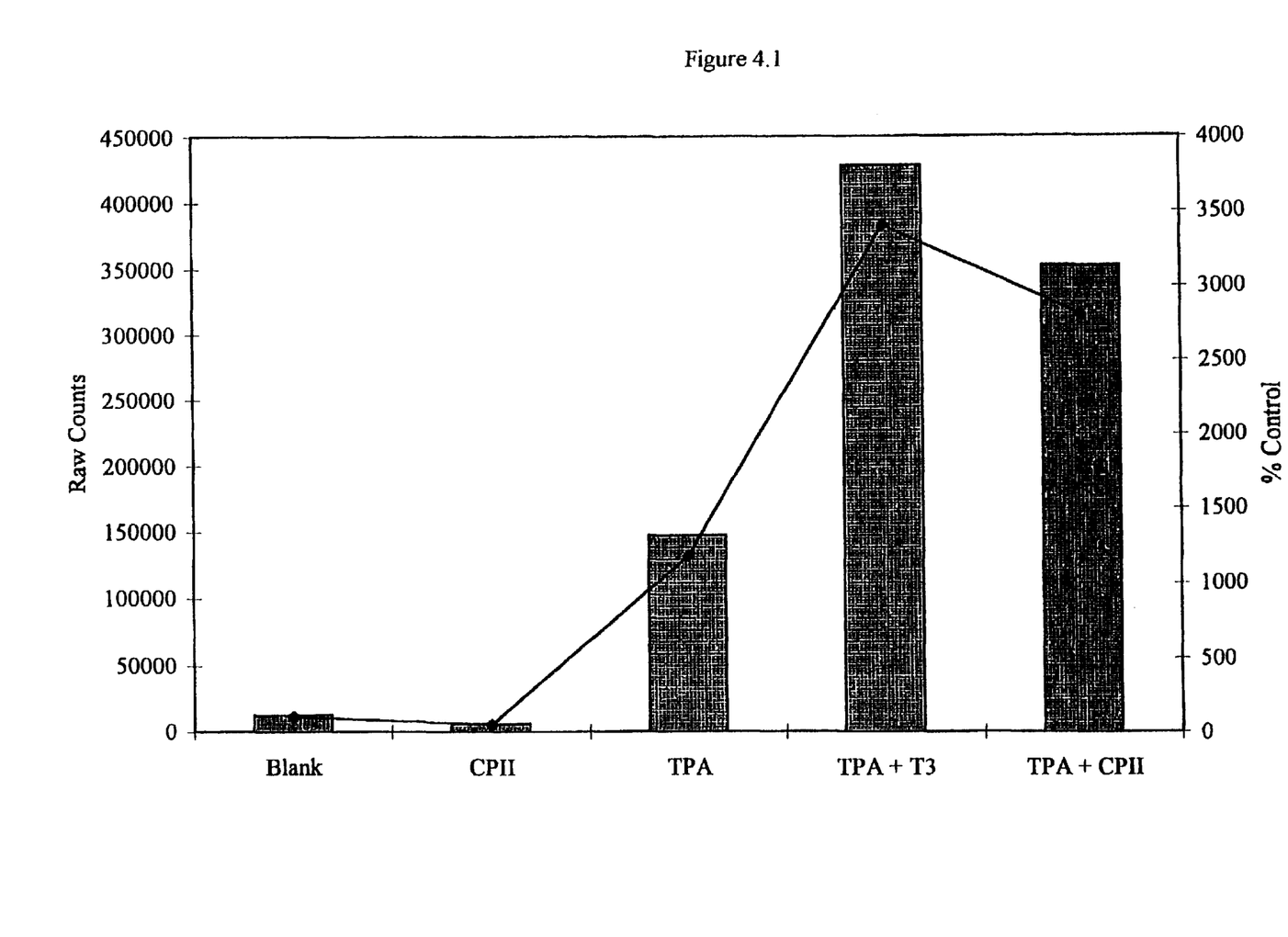

The results in Table 4. 1, presented graphically in FIG. 4.1, show that in MCF-7 cells, both thyroid hormone and Compound II are able further to enhance TPA stimulation of luciferase production.

EXPERIMENT 4.2.

The procedure of Experiment 4.1 was repeated except that a second plasmid, containing 662bp antisense construct for the thyroid receptor (at 8 ug per $5 \times 10^5$ cells) was additionally transfected.

The results are shown in Table 4.2.

TABLE 4.2

|  | Raw Counts | % Control |
| --- | --- | --- |
| Blank | 1458 | 100 |
| CPII | 2379 | 163.2 |
| TPA | 4975 | 341.2 |
| TPA + T3 | 19911 | 1365.6 |
| TPA + CPII | 8716 | 597.8 |

Figure 42:
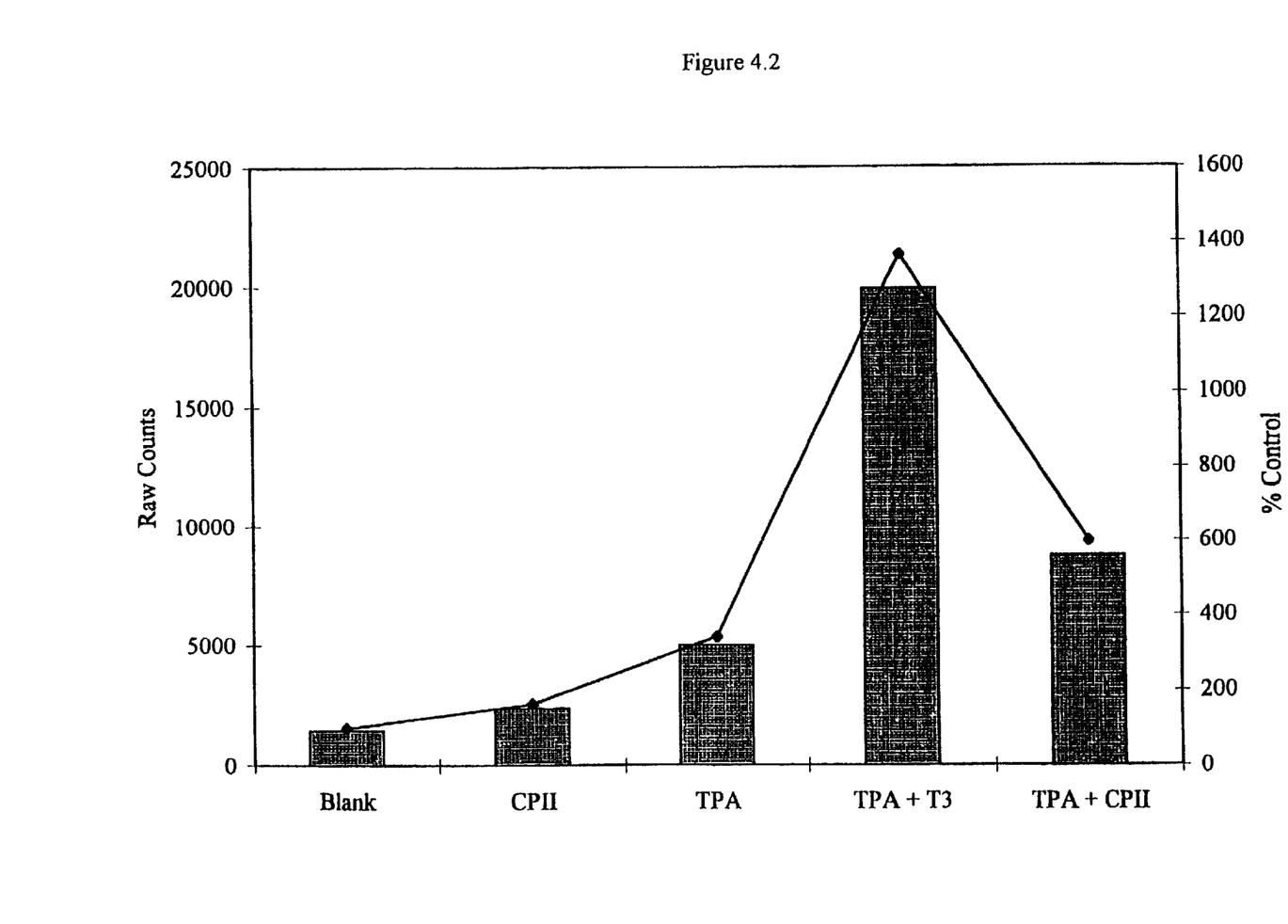

The results in Table 4.2, presented graphically in FIG. 4.2, show that when the thyroid hormone receptor synthesis is inhibited, luciferase production via the action of T3 and compound II is substantially prevented.

EXPERIMENT 4.3.

A second plasmid was introduced containing pSP71 vector (Promega) (at 2 ug per $5 \times 10^5$ cells) containing the coding sequence for the chick thyroid hormone receptor which shows high homology to the human thyroid hormone receptor, driven by the Rous sarcoma virus promoter to ensure constitutive production.
The results are shown in Table 4.3

TABLE 4.3

|  | Raw Counts | % Control |
| --- | --- | --- |
| Blank | 2183 | 100 |
| CPII | 1572 | 72 |
| TPA | 11528 | 528 |
| TPA + T3 | 1604 | 73 |
| TPA + CPII | 4414 | 202 |

Figure 43:
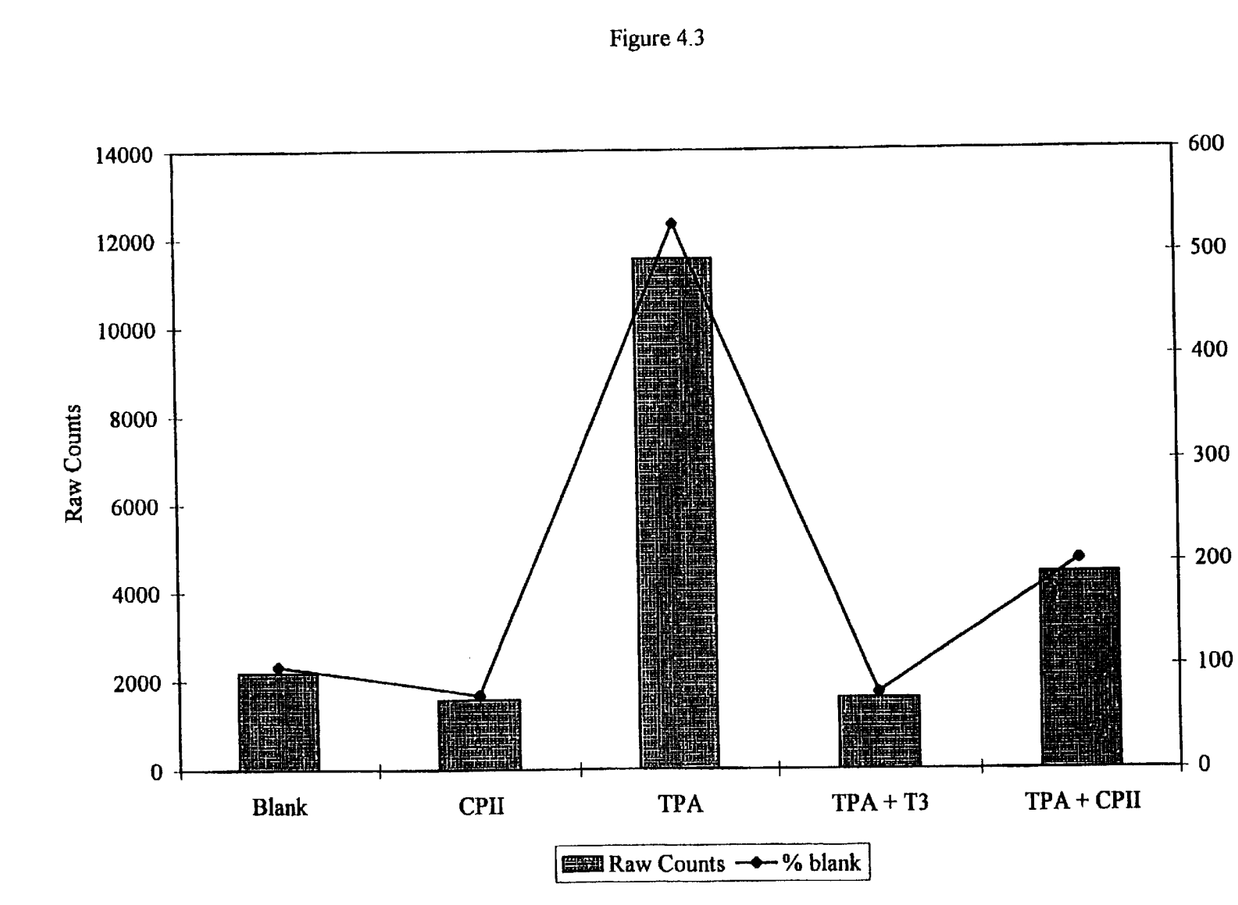

The results in Table 4.3, presented graphically in FIG. 4.3, show that Compound II, as well as thyroid hormone, is able to reduce stimulated collagenase transcription.

Taken together, the results of Experiments 4.1, 4.2 and 4.3 show that compound II mimics the action of T3 which is a known ligand for the thyroid hormone receptor.

EXPERIMENT 5

This experiment was designed to demonstrate down-regulation of pro-MMP-1 and phosphorylation at serine 73 of c-jun, the latter of which is one half of the protein dimer AP-1, a key regulator of metalloprotease expression.

METHODS

Rheumatoid fibroblasts were cultured from synovium obtained from the knee joint of a patient with rheumatoid arthritis. Cells were cultured in monolayer with DMEM tissue culture medium (Gibco) with the inclusion of 5%v/v charcoal stripped serum in 75 cm² flasks. The cells were treated for 36 hours with the addition of 10 ng/ml TPA (phorbol ester) plus $5 \times 10^{-7}$M thyroid hormone, Compound II or Compound III. TPA and drugs were added at time zero and at 30 hours, the TPA addition ensured phosphorylation of c-jun.

After 36 hours, cells were lysed in phosphate buffered saline (PBS) containing protease inhibitors and 0.1% Triton-X- 100, and then boiled for 5 minutes in non-reducing gel loading buffer. Samples of cell lysate corresponding to equal cell number were loaded onto a 12.5% SDS polyacrylamide gel, and electrophoresis using a Bio-Rad™, (Bio-Rad Laboratories, California USA) Mini Protean II cell was performed at approximately 100V for one hour.

Transfer of proteins to nitrocellulose membrane was performed using a Bio-Rad Mini Trans-Blot transfer cell.

Immunoblotting was performed using polyclonal rabbit anti-human phosphorylation specific (ser 73) c-jun (cat. No 06659, Upstate Biotechnology), or MMP-1 (cat. No. RDI-MMP1Habr, Research Diagnostics) antibodies diluted 1:1000 in Tris buffered saline+3% fat free milk powder. Swine anti-rabbit horseradish peroxidase conjugated antibody, (cat. No. p0217, Dako) also at 1:1000 dilution was used as the secondary antibody. Chemiluminescent detection was employed using Amersham reagents according to manufacturer's instructions. Visualisation was achieved by exposing the membrane to X-ray film (Kodak) for one hour.

Figure 5:
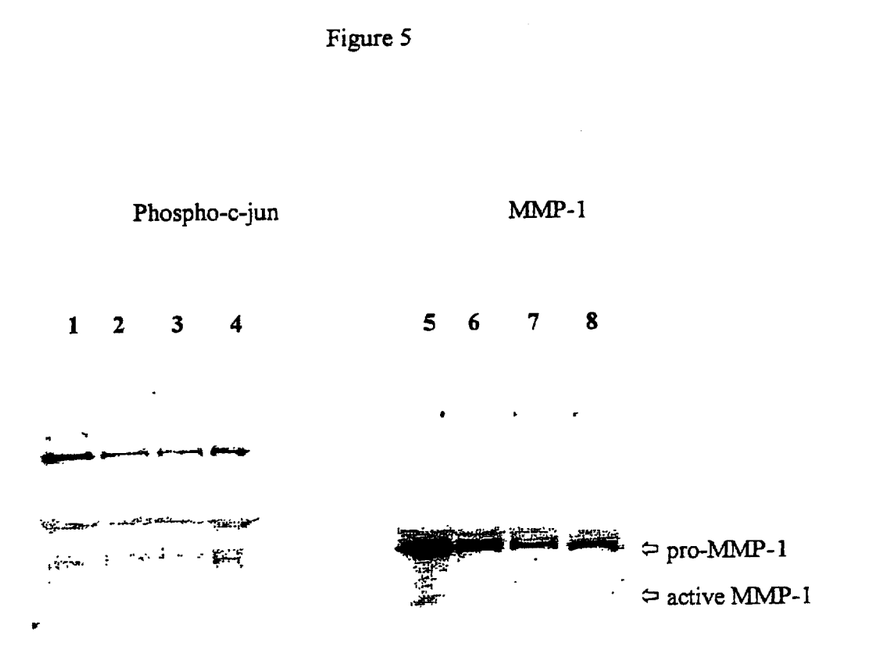

Results are shown in FIG. 5. Left side column of the figure shows bands corresponding to phosphorylated c-jun (at serine 73), completed with DNA, at the top of the figure. Right hand side column demonstrates a strong related band corresponding to pro-MMP1 and a faint band at a lower molecular weight corresponding to active-MMP-1. Lanes 1 and 5 cells treated with TPA alone; Lanes 2 and 6 cells treated TPA plus thyroid hormone; Lanes 3 and 7 cells treated with TPA plus Compound II; Lanes 4 and 8 cells treated with TPA plus Compound III.

Lanes 2, 3 and 4 show a lower intensity and therefore, amount of phosphorylation of c-jun, when compared to the TPA alone treated control in lane 1. Similarly, lanes 6, 7 and 8 show a lower intensity and therefore, a lower amount of pro-MMP-1, when compared to the TPA alone treated control in lane 5. Since the lower molecular weight band across lanes 5, 6, 7 and 8 corresponding to active MMP-1 is very faint, the regulation by thyroid hormone, and Compounds II and III appears to be occurring at the transcriptional level to produce a similar effect to thryoid hormone on the expression of pro-MMP-1.

SUMMARY

Compound II, typical of compounds I, demonstrated steroid like properties in its ability to reduce collagenase promoter activity, although this was evident in the substantive absence of glucocorticoid or androgen receptors. Additionally, compound II did not activate a construct designed to show responsiveness to the glucocorticoid receptor. It did not enhance or block the activity of an immune system mediator, demonstrating that it does not possess anti-inflammatory properties, neither does it compromise immune response signalling. In a further experiment, the activity of compound II was identical to T3 in the absence and presence of endogenous or transfected thyroid hormone receptor. This demonstrated a common mechanism for these two molecules. The liganded thyroid hormone receptor is known to be able to down regulate collagenase promoter activity (A novel mechanism of action for v-ErbA: abrogation of the inactivation of transcription factor AP-1 by retinoic acid and thyroid hormone receptors, Desbois-C; Aubert-D; Legrand-C; Pain-B, Samarut-J Cell. Nov. 15, 1991 67(4): 731–40), although the mechanism by which this occurs has not yet been elucidated.

What is claimed is:

1. A method of alleviating loosening of prosthetic joints by reducing bone degradation in the joint which comprises administering an effective amount of at least one compound having the formula (I)

(I)

in which X stands for the oxygen or sulphur atom or for the imino (—NH—) or sulphonyl (—SO$_2$—) radical, Y stands for a direct linkage, or for the oxygen or sulphur atom or for the sulphonyl (—SO$_2$—) radical or for the radical of the formula —CR$^1$R$^2$—, wherein R$^1$ and R$^2$ which may be the same or different are hydrogen, alkyl or aryl radicals or R$^1$ and R$^2$ may be joined together to form a cycloalkyl ring, and ring B may be optionally substituted by one or more substituents selected from halogen atoms and alkyl and aryl radicals, when n is an integer having the value 1, or Y stands for the oxygen or sulphur atom or for the sulphonyl (—SO$_2$—) radical, ring B may be optionally substituted by one or more substituents selected from halogen atoms and alkyl and aryl radicals when n has the value 0, or an ester, amide or salt thereof.

2. A method as claimed in claim 1 in which R$^1$ is selected from hydrogen and 1–4C alkyl, R$^2$ is selected from hydrogen, 1–4C alkyl and phenyl which may optionally be substituted by at least one halogen atom, or R$^1$ and R$^2$ may be joined together to form a cyclohexyl ring, and ring B may optionally contain one or more substituents selected from halogen atoms and 1–4C alkyl.

3. A method as claimed in claim 2 in which the compound has the formula II

(II)

4. A method as claimed in claim 2 in which the compound has the formula (III)

(III)

5. A method as claimed in claim 2 in which the compound has the formula (IV)

(IV)

* * * * *